(12) United States Patent
Comings et al.

(10) Patent No.: US 6,897,212 B2
(45) Date of Patent: May 24, 2005

(54) TREATMENT OF OPPOSITIONAL DEFIANT DISORDER AND CONDUCT DISORDER WITH 5-AMINOALKYL-4,5,6,7-TETRAHYDRO-4-OXYINDOLONES

(75) Inventors: David E. Comings, Monrovia, CA (US); Bruce Kovacs, Long Beach, CA (US); Jim MacMurry, Claremont, CA (US)

(73) Assignee: Afecta Pharmaceuticals, Irvine, CA (US)

( * ) Notice: Subject to any disclaimer, the term of this patent is extended or adjusted under 35 U.S.C. 154(b) by 0 days.

(21) Appl. No.: 10/431,491

(22) Filed: May 7, 2003

(65) Prior Publication Data

US 2004/0116502 A1 Jun. 17, 2004

Related U.S. Application Data

(63) Continuation-in-part of application No. 10/126,065, filed on Apr. 19, 2002, now Pat. No. 6,613,763.

(51) Int. Cl.$^7$ ...................... A61K 31/535; A61K 31/40
(52) U.S. Cl. .................................... 514/232.8; 514/412
(58) Field of Search ............................. 514/232.8, 412

(56) References Cited

U.S. PATENT DOCUMENTS

| | | | |
|---|---|---|---|
| 3,491,093 | A | 1/1970 | Pachter |
| 4,065,453 | A | 12/1977 | Finizio |
| 5,663,167 | A | 9/1997 | Pickar et al. |
| 6,028,070 | A | 2/2000 | Heiligenstein |
| 6,090,829 | A | 7/2000 | Bodick et al. |
| 6,136,824 | A | 10/2000 | MacLeod et al. |
| 6,184,222 | B1 | 2/2001 | Heiligenstein |
| 6,210,950 | B1 | 4/2001 | Johnson et al. |
| 6,214,846 | B1 | 4/2001 | Elliott |
| 6,613,763 | B2 * | 9/2003 | Comings et al. ......... 514/232.8 |

OTHER PUBLICATIONS

Greenhill et al. J. Clin. Psychiatry, (Aug. 1985), 46 (8 Pt. 2) pp 20–25 Abstract Only.*
S. Leucht et al., "Therapeutics Review: in people wit schizophrenia, lithium is ineffective.," Evidence–Based Mental Health, 2004; 7: 104. EMBH Online.
S. Leucht et al., "Lithium for schizophrenia (Cochrane Review)," The Cochrane Library, Issue 4, 2004. ABSTRACT.
Dr. Joseph F. Smith Medical Library, Delusions. (2004).
Physicians' Desk Reference, Edition 55, 2001. Lithium Carbonate, p. 2827.
Ravina, Enrique et al., "Conformationally constrained butyrophenones. . . ," Current Medicinal Chemistry—Central Nervous System Agents, May 2001, vol. 1, No. 1, pp. 43–62.
Laurence L. Greenhill et al., "Molindone Hydrochloride in the treatment of aggressive, hospitalized children," pp. 125–127. XP008019356. (no date available).
Laurence L. Greenhill et al., "Molindone Hydrochloride in the treatment of hospitalized children with conduct disorder," J.Clin.Psychiatry, Aug. 1985, 46 : 8 (Sec. 2), pp. 20–25. XP008019351.
Richard R. Owen et al., "Molindone Hydrochloride: A review of laboratory and clinical findings," J. Clin. Pyschopharmacology, Aug. 1989, vol. 9, No. 4. pp. 268–276.
Priscille Gerardin et al., "Drug treatment of conduct disorder in young people," European Neuropsychopharmacology, 2002, vol. 12, pp. 361–370. XP–002246780.
"Letters to the Editor," J.Am.Acad.Child Adolesc. Psychiatry, Jan. 1997, 36:1, pp. 1–3. XP008019353.
Elizabeth B. Weller, M.D. et al., "Aggressive behavior in patients with attention–deficit/hyperactivity disorder, conduct disorder, and pervasive development disorders," J.Clin. Psychiatry, 1999, 60 (suppl 15), pp. 5–11. XP008019349.

* cited by examiner

*Primary Examiner*—Raymond J. Henley, III
(74) *Attorney, Agent, or Firm*—Birch, Stewart, Kolasch & Birch, LLP

(57) ABSTRACT

A method for treating the psychiatric disorders known as oppositional defiant disorder and conduct disorder is disclosed. The method comprises the administration of a compound according to Formula I or II to a patient suffering from oppositional defiant disorder and/or conduct disorder. The compound may be either a racemic mixture or e.g. the levorotatory form. It may be short acting or in a sustained release, long acting form. Molindone or a pharmaceutically acceptable salt of molindone is a preferred embodiment.

17 Claims, No Drawings

TREATMENT OF OPPOSITIONAL DEFIANT DISORDER AND CONDUCT DISORDER WITH 5-AMINOALKYL-4,5,6,7-TETRAHYDRO-4-OXYINDOLONES

This application is a continuation-in-part of application Ser. No. 10/126,065 filed on Apr. 19, 2002, now U.S. Pat. No. 6,613,763, the entire contents of which are hereby incorporated by reference and for which priority is claimed under 35 U.S.C. § 120.

Oppositional defiant disorder (ODD) and Conduct disorder (CD) are two of the most common psychiatric disorders affecting children and adolescents. Rates of ODD range from 2 to 16% depending on the nature of the population sample and methods of ascertainment. Rates of CD are in the same range. This translates into many millions of cases. The Diagnostic and Statistical Manual of Mental Disorders, 4th edition (DSM-IV) characteristics of ODD include short temper, constant arguing with adults, defying rules, deliberately annoying others, blaming others for their own mistakes, being angry and resentful, spiteful and vindictive. In its severe form such children can be highly destructive to family life. Despite these characteristics no pharmaceutical companies market any medications specifically for ODD, and the majority of child psychiatrists feel it is largely a psychological disorder and make no effort to treat it medically.

The Diagnostic and Statistical Manual of Mental Disorders, 4th edition (DSM-IV) characteristics of CD are a repetitive and persistent pattern of behavior in which the basic rights of others or major age-appropriate norms or rules are violated, as manifested by the presence of three or more of a range of criteria for 12 months. These include aggression to people and animals (bullying, threatening, starting fights, using a weapon to cause harm, being cruel to animals or people, stealing, forcing others into sexual activity), destruction of property, fire setting, deceitfulness or theft (breaking into homes or property, stealing things of value), and serious violation of rules (staying out over night when less than 13 years of age, running away from home, truant from school before age 13).

The instant invention is the finding that ODD and CD can be treated with certain indol compounds, including dihydroindolones and in particular the drug molindone (Moban) which is a short acting a typical antipsychotic, and derivatives thereof. Molindone is a dihydroindolone neuroleptic which is structurally distinct from other classes of neuroleptics. It exhibits many similarities to other neuroleptics, including dopamine receptor blockade, antipsychotic efficacy, and extrapyramidal side effects, yet molindone has a typical properties such as inhibiting the enzyme monoamine oxidase. Molindone is generally used for the treatment of schizophrenia and other psychotic disorders. Studies have been published in which molindone was tested for treatment of schizophrenia, anxiety and depression, and conduct disorder.

The publications and other materials used herein to illuminate the-background of the invention or provide additional details respecting the practice, are incorporated by reference, and for convenience are respectively grouped in the appended List of References.

The present invention refers to the use of an indole compound I for the manufacture of a medicament for treating oppositional defiant disorder and/or conduct disorder wherein said indole compound I is represented by general formula I

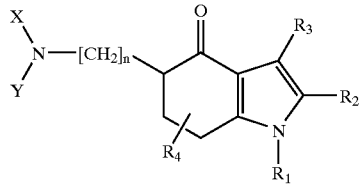

wherein:

n is 1, 2 or 3;

$R_1$ designates hydrogen, a lower alkyl, benzyl, phenyl or 2-, 3- or 4-pyridyl;

$R_2$ and $R_3$ are each independently alkyl, alkenyl and cycloalkyl, phenyl, halogeno-phenyl or lower alkoxy phenyl;

$R_4$ designates hydrogen or a lower alkyl and being attached to carbon atom 6 or 7 of the indole nucleus; and X and Y designate lower alkyl, hydroxy lower alkyl, lower acyloxy alkyl, carbamoyloxy lower alkyl and phenyl lower alkyl or alternatively X and Y may be linked together and then constitute, together with the nitrogen atom to which they are attached, an NXY moiety that is an optionally substituted heterocyclic ring;

or is a pharmaceutically acceptable acid addition salt thereof.

Furthermore, the invention provides the use of an indole compound I for the manufacture of a medicament for treating oppositional defiant disorder and/or conduct disorder wherein said indole compound I is represented by general formula I

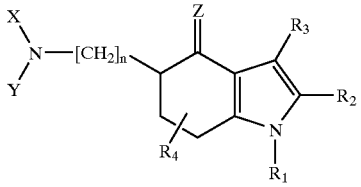

wherein:

n is 1, 2 or 3;

$R_1$, $R_2$, $R_3$ and $R_4$ are each independently a hydrogen, alkyl, a alkenyl or a alkynyl radical optionally substituted by 1–3 radicals of amino, alkylamino, dialkylamino, alkanoylamino, alkoxycarbonylamino, alkylsulfonylamino, a hydrogen atom, hydroxy, alkoxy, alkylthio, an alkylsulfinyl group, a lower alkylsulfonyl group, halo, a carboxyl group, a lower alkoxy-carbonyl group, a benzyloxycarbonyl group, a cyano group, a benzyloxy group, a lower alkanoyloxy group, a cycloalkyl group, a cycloalkyl group, an aryl group, an aralkyl group, a substituted aryl group, a heteroaryl group, a substituted heteroaryl group, a benzenesulfonyloxy group being optionally substituted by an alkyl group; a lower alkanoylamino group, a lower alkoxycarbonylamino group, a lower alkylsulfonamido group, a phthalimido group;

or $R_3$ is also one or more members selected from the group consisting of hydrogen, amino, alkylamino, dialkylamino, alkanoylamino, alkoxycarbonylamino, and alkylsulfonylamino;

X and Y designate lower alkyl, hydroxy lower alkyl, lower acyloxy alkyl, carbamoyloxy lower alkyl and phenyl lower alkyl, or X and Y may be linked together and then constitute, together with the nitrogen atom to which they are attached, an NXY moiety that is an optionally substituted heterocyclic ring; and Z is selected from the group consisting of oxo, thio, seleno, telluro, and NH;

or is a pharmaceutically acceptable acid addition salt thereof.

In yet another embodiment, the invention relates to the use of a dihydroindolone derivative of molindone or a pharmaceutically acceptable acid addition salt of said derivative for the preparation of a medicament for oppositional defiant disorder.

5-Aminoalkyl-4,5,6,7-tetrahydro-4-oxyindolones are a family of compounds that are comprised of the dihydroindolones, including molindone and derivatives thereof. It has been found that these compounds are useful for the treatment of oppositional defiant disorder and conduct disorder. Use of a preferred dose of 1.25 to 10 mg every 4 hours eliminates the symptoms of ODD or CD with minimal or no side effects.

Oppositional Defiant Disorder

Oppositional Defiant Disorder is one of the most common psychiatric disorders affecting children and adolescents. Rates of ODD range from 2 to 16% depending on the nature of the populations sample and methods of ascertainment. The place of ODD in the classification system was controversial when first introduced by the Diagnostic and Statistical Manual of Mental Disorders, Third Edition, revised (DSM-III-R) (American Psychiatric Association 1987). According to Rey (1993), some authors questioned whether oppositional defiant disorder was sufficiently distinct from normal oppositional behavior to warrant its inclusion as a distinct diagnostic category (Rutter and Shaffer, 1980) while other authors argued that the criteria for ODD implied a milder form of conduct disorder (Werry et al., 1983; Werry et al., 1987). Despite this early controversy, ODD has become one of the diagnoses more commonly made in clinical setting and community samples (Rey, 1993).

Probably as a result of the original controversy concerning whether ODD was a distinct diagnostic category, the concept of ODD underwent considerable changes. DSM-III introduced oppositional disorder in the category Disorders Usually First Evident in Infancy, Childhood or Adolescence to describe children who show a persistently disobedient, negativistic, and provocative opposition to authority figures, manifested by at least two of the following symptoms: 1) violations of minor rules, 2) temper tantrums, 3) argumentativeness, 4) provocative behavior, and 5) stubbornness. This diagnosis was placed under the heading Other Disorders of Infancy, Childhood and Adolescence, together with diagnoses such as schizoid disorder, elective mutism, and identity disorder (Rey, 1993). The International Classification of Diseases 9 (ICD-9 (World Health Organization)) did not contain a comparable diagnosis. Seven years later, DSM-III-R changed the name to oppositional defiant disorder and placed it, together with conduct disorder and attention deficit hyperactivity disorder, under the heading Disruptive Behavior Disorders (Rey, 1993). The number of diagnostic criteria was increased to nine by the addition of 1) blames others for his or her own mistakes, 2) is touchy or easily annoyed, 3) is angry and resentful, 4) is spiteful or vindictive, and 5) swears, and by the removal of stubbornness; the remaining four criteria were reworded (e.g., temper tantrums became "often loses temper") (Rey, 1993). Also, the number of criteria required for the diagnosis was increased to five. These modifications were designed to counter the criticism that ODD could not be distinguished from the behavior of many normal children and the changes were well received (Rey, 1993; Rutter, 1988). In both DSM-III and DSM-III-R, a diagnosis of oppositional defiant disorder can be made only in the absence of conduct disorder (Rey, 1993).

The 4th edition of the Diagnostic and Statistical Manual of Mental Disorders (DSM-IV) 5 came into use in 1994 (American Psychiatric Association, 1994). It defines the essential feature of ODD as a recurrent pattern of negativistic, defiant, disobedient, and hostile behavior toward authority figures that persists for at least 6 months (Criterion A) and is characterized by the frequent occurrence of at least four of the following behaviors: losing temper (Criterion A1), arguing with adults (Criterion A2), actively defying or refusing to comply with the requests or rules of adults (Criterion A3), deliberately doing things that will annoy other people (Criterion A4), blaming others for his or her own mistakes or misbehavior (Criterion A5), being touchy or easily annoyed by others (Criterion A6), being angry and resentful (Criterion A7), or being spiteful or vindictive (Criterion A8). To qualify for ODD, the behaviors must occur more frequently than is typically observed in individuals of comparable age and developmental level and must lead to significant impairment in social, academic, or occupational functioning (Criterion B). The diagnosis is not made if the disturbance in behavior occurs exclusively during the course of a Psychotic or Mood Disorder (Criterion C) or if criteria are met for Conduct Disorder or Antisocial Personality Disorder (in an individual over age 18 years) (DSM-IV, American Psychiatric Association, 1994) Although ODD includes some of the features observed in Conduct Disorder (e.g., disobedience and opposition to authority figures), it does not include the persistent pattern of the more serious forms of behavior in which either the basic rights of others or age-appropriate societal norms or rules are violated (DSM-IV, American Psychiatric Association, 1994). When the individual's pattern of behavior meets the criteria for both Conduct Disorder and ODD, the diagnosis of Conduct Disorder takes precedence and ODD is not diagnosed (DSM-W, American Psychiatric Association, 1994). ICD-10 (World Health Organization, 1992) also includes a category of oppositional defiant disorder, defined by the presence of markedly defiant, disobedient, provocative behavior in the absence of severe dissocial or aggressive acts that violate the law or the rights of others. ICD-b conceptualizes oppositional defiant disorder as part of the dimension of conduct disorder (Rey, 1993). For the diagnosis of ODD, ICD-b requires that the child meet two of three criteria (frequent and marked lying, excessive fighting, and defiance of adult requests and commands) and not meet any of the other 12 criteria for conduct disorder (World Health Organization, 1990). Rey (1993) outlines the developmental patterns of both ODD and conduct disorder with the following being taken from the Rey (1993) publication. There is a substantial body of research showing that symptoms of oppositional defiant disorder typically appear during the preschool years, when they are considered normal (Rey, 1993). Temper tantrums reach their peak when children are 2–3 years of age (Goodenough, 1931; Shepherd et al., 1971). During the preschool years negativistic and oppositional behavior is common, resulting in angry outbursts and ensuing conflicts with parental authority about matters that vary with age, such as toilet training or possessions at age 2 and tidiness at age 5 (Rey, 1993). Destructiveness, bullying, and fighting decrease after the preschool years (Rutter and Oiler, 1983). Early adolescence is often associated with an increase in rebellious behavior (Looney and Oldham, 1989). Teachers' reports indicate that most oppositional symptoms, such as arguing, screaming, disobedience, and defiance, peak between the ages of 8 and 11 years and then decline in frequency (Achenbach and Edelbrock, 1986). According to parents, swearing and argumentativeness become more prevalent during adolescence, particularly among girls (Achenbach, 1991). By contrast, most symptoms of conduct disorder (truancy, stealing, drug and alcohol use, etc.), with the exception of lying, do not occur during the preschool years but become increasingly frequent during late childhood and adolescence (Rutter and Giller, 1983; Looney and Oldham, 1989; Achenbach and Edelbrock, 1986; Achenbach, 1991; Loeber et al., 1991). Boys are significantly more aggressive than girls, but sex differences change with age: they are large in 4- to 5-year-olds, moderate in 9- to 12-year-olds, and small in college students (Cohn, 1991). Thus, developmental patterns of behavior in oppositional defiant disorder and conduct disorder appear to follow a different course (Lahey et al., 1992). This indicates that ODD and conduct disorder are in fact distinct from each other.

Several clinicians and researchers have expressed the belief that ODD is a mild form of conduct disorder (Rutter and Shaffer, 1980; Werry et al., 1987), but this issue has been reviewed (Loeber et al., 1991; Quay, 1986) with the authors of the reviews concluding that there is considerable agreement across factor analytical studies in the finding that symptoms of disruptive behavior consistently aggregate in two groupings: one consists of all oppositional defiant disorder behavior plus some symptoms of mild physical aggression, such as fighting and bullying, while the other consists of covert, nonaggressive conduct disorder behavior, such as stealing, truancy, and running away (Rey, 1993). This aggregation into two groupings further enforces the idea that ODD and conduct disorder are distinct from each other. Loeber et al. (1991) stated that the possible distinction between ODD and conduct disorder (CD) can be conceptualized in at least three ways: (a) the diagnostic categories may be entirely distinct entities; (b) they may be more or less severe expressions of the same etiology, wherein some youths progress over time from the less severe symptoms (ODD) to the more severe symptoms (CD); or (c) ODD and CD may be largely distinct disorders with partially related etiologies. The authors addressed these alternative conceptualizations by reviewing evidence on patterns of behavioral covariation, age of onset, the developmental course, correlates and risk factors, stability and predictability, seriousness ratings, and treatment implications (Loeber et al., 1991). The conclusions which were reached include the following: 1) in terms of behavioral covariation, much of the literature suggests that most symptoms of CD and ODD are distinct; 2) the mean age of onset for ODD symptoms is earlier than that for CD symptoms; 3) the familial correlates of ODD and CD are very similar in terms of history of antisocial behavior and family adversity, but youths with CD tend to show a larger number of these correlates than youths with ODD; 4) developmentally, ODD symptoms predict CD symptoms, in analogy with CD's predicting antisocial personality; with the authors stating that in general, the various vantage points reviewed suggest that ODD and CD are different disorders although developmentally related (Loeber et al., 1991).

Rey (1993) discusses several more aspects of ODD including diagnosis, epidemiology, comorbidity, validity, etiology and treatment. The reliability of the diagnosis was found to depend upon the diagnostic criteria. A threshold of five criteria fulfilled had the best combination of sensitivity (80%) and specificity (79%), discriminating between patients with and without ODD (Rey, 1993; Spitzer et al., 1990). Studies of ODD in community samples based on the use of specified criteria—mostly those of DSM-III—and standardized interviews show a prevalence of ODD between 1.7% and 9.9%, with a weighted average of 5.7%. Approximately one-third of all of the children with any disorder had a diagnosis of ODD (Rey, 1993; Anderson et al., 1987; Kashani et al., 1987; Cohen et al., 1987; Bird et al., 1988; McGee et al., 1990). Overall, ODD is diagnosed more often in boys than in girls although this depends on the age of the child, studies of children 12 years of age or younger showing a prevalence of ODD in boys double that seen in girls (Anderson et al., 1987; Cohen et al., 1987) while studies of adolescents (Kashani et al., 1987; Cohen et al., 1987; McGee et al., 1990) showed a higher prevalence of ODD in girls. These changes parallel those reported for aggressive behavior (Cohn, 1991). By comparison, conduct disorder was diagnosed more often in boys in all age groups in most studies (Rey, 1993). This difference is yet further confirmation of the distinction between ODD and conduct disorder.

Studies trying to assess the effect of age on ODD are contradictory with one study (Cohen et al., 1987) showing an increase of ODD with increased age while another (McGee et al., 1990) showed a decline. Another study (Pelham et al., 1992) reported a gradual increase in ODD with increasing age in a community sample. By contrast, there is little doubt that conduct disorder becomes more prevalent during adolescence (Rey, 1993). There is a high comorbidity between ODD and attention deficit hyperactivity disorder and also a high comorbidity between ODD and conduct disorder (Rey, 1993). Some overlap was seen between ODD and separation anxiety, generalized anxiety disorder and major depressive disorder and there appears to be an association between ODD and communication disorders (Rey, 1993). It is unresolved whether comorbidity between ODD and conduct disorder is higher than between ODD and other disorders. Having one psychiatric disorder increases the probability of having a second disorder (Caron and Rutter, 1991; Robins et al., 1991), therefore a specific association between oppositional defiant disorder and another disorder can be assumed only if comorbidity is significantly higher than that expected when another diagnosis is present. The diagnosis of ODD remains stable over time. Cantwell and Baker (1989) did a 4-year follow-up study of a group of children who had been diagnosed as suffering from DSM-III disorders and found that ODD, together with autism and attention deficit hyperactivity disorder, was one of the most stable diagnoses. ODD also showed the poorest recovery rate of all the behavioral psychiatric disorders (Rey, 1993). This underscores the need for an effective medication for persons diagnosed with ODD.

The stability of ODD was shown in two more studies. Cohen et al. (1991) showed that a diagnosis of ODD predicted a significant increase in the use of mental health services 2 years later. A follow-up study of children with attention deficit hyperactivity disorder into adolescence reported that most differences between children with attention deficit hyperactivity disorder and normal control subjects were attributable to the group with comorbid ODD at follow-up (Barkley et al., 1991). The degree of aggression in childhood predicted symptoms of ODD in adolescence, and these were very stable (Rey, 1993). These findings show that children with ODD do not necessarily develop conduct disorder when they grow older (Rey, 1993; Lahey et al., 1992; Cantwell and Baker, 1989). As of 1993, Rey (1993) reports that no study was identified that used medication for children with ODD. Rey (1993) states that it is widely accepted that response to treatment of patients with conduct disorder is very poor, citing Kazdin (1987), and that if it were shown that children with ODD respond to specific treatments more consistently than those with conduct disorder then there would be even greater support that ODD and conduct disorder are different from each other. Loeber (1991) published an article contrasting ODD and conduct disorder. This reference states that symptoms of ODD can resemble normal problem behaviors, but the symptoms of ODD are distinguished from normal behavioral problems if they occur at a rate and intensity that is a typical for the child's age group or persist through a later age than for most youngsters.

In contrast, symptoms of conduct disorder are usually considered undesirable at any period in a youngster's life because they tend to result in personal harm or property loss or damage (Loeber, 1991). Symptoms of ODD consist of overt or conirontive problem behaviors, while most conduct disorder symptoms, such as theft and truancy, are of a covert, concealing nature (Loeber, 1991). Furthermore, the developmental course of ODD generally differs from that of conduct disorder. Symptoms of ODD usually appear before the onset of the majority of conduct disorder symptoms whereas serious overt conduct disorder symptoms, such as rape and mugging, tend to emerge during late adolescence and early adulthood (Loeber, 1991). According to Loeber (1991), early onset of serious theft or substance use predicts a high persistence, variety, and seriousness of conduct problems later, but early onset does not appear to indicate persistence of ODD symptoms. Also, the prevalence of symptoms of the two disorders changes over time in an orderly fashion, with the prevalence of ODD in samples not referred for treatment decreasing with age whereas by contrast the prevalence of several conduct disorder symptoms increases from middle childhood onward and accelerates in adolescence (Loeber, 1991).

A study was performed recently to determine whether ODD is a precursor to conduct disorder (Biederman et al., 1996). To perform the study, assessments from multiple domains were used to examine 140 children with attention-deficit hyperactivity disorder (ADHD) and 120 normal controls at baseline and 4 years later. It was seen that of all children who had ADHD at baseline, 65% had comorbid ODD and 22% had CD. Among those with ODD, 32% had comorbid CD. All but one child with CD also had ODD that preceded the onset of CD by several years. ODD plus CD children had more severe symptoms of ODD, more comorbid psychiatric disorders, lower Global Assessment of Functioning Scale scores, more bipolar disorder, and more abnormal Child Behavior Checklist clinical scale scores compared with ADHD children with non-CD ODD and those without ODD or CD. In addition, ODD without CD at baseline assessment in childhood did not increase the risk for CD at the 4-year follow-up, by mid-adolescence. It is concluded that two subtypes of ODD associated with ADHD were identified: one that is prodromal to CD and another that is subsyndromal to CD but not likely to progress into CD in later years (Biederman et al., 1996).

5-Aminoalkyl-4,5,6,7-tetrahydro-4-oxyindolones

The 5-aminoalkyl-4,5,6,7-tetrahydro-4-oxyindolones can be represented by formula I as set forth below:

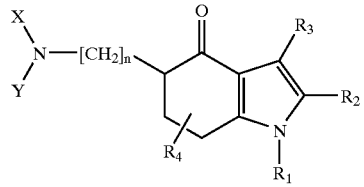

n is 1, 2 or 3.

$R_1$ designates hydrogen, a lower alkyl, benzyl, phenyl or 2-, 3- or 4-pyridyl. Preferably $R_1$ is hydrogen or a lower alkyl.

$R_2$ and $R_3$ are each independently alkyl, alkenyl, cycloalkyl, phenyl, halogeno-phenyl or lower alkoxy phenyl. Preferably $R_2$ and $R_3$ are each independently alkyl, more preferably lower alkyl.

$R_4$ designates hydrogen or a lower alkyl and is attached to carbon atom 6 or 7 of the indole nucleus. Preferably $R_4$ is hydrogen.

X and Y designate lower alkyl, hydroxy lower alkyl, lower acyloxy alkyl, carbamoyloxy lower alkyl and phenyl lower alkyl. Alternatively X and Y may be linked together and then constitute, together with the nitrogen atom to which they are attached, an NXY moiety that is an optionally substituted heterocyclic ring. In one preferred embodiment X and Y are a lower alkyl or phenyl lower alkyl. In a second preferred embodiment X and Y are linked together and then constitute, together with the nitrogen atom to which they are attached, an NXY moiety that is a heterocyclic ring. Preferably in this embodiment NXY is a morpholinyl group, a pyrrolidyl group, imidazolidinyl group, a piperidyl group or a piperazinyl group, each of which can be substituted; more preferably NXY is a morpholinyl group, a piperidyl group or a piperazinyl group, each of which can be substituted (e.g. by a lower alkyl group, a lower alkoxy group or a phenyl group optionally substituted with a hydroxy group or a lower alkyl group or a lower alkoxy group).

The 5-aminoalkyl-4,5,6,7-tetrahydro-4-oxyindolones or a pharmaceutically acceptable acid addition salt of said compound (I) may be administered according to the present invention for the treatment of oppositional defiant disorder and/or conduct disorder.

Racemic mixtures as well as enantiomers and diastereomers can be employed.

Molindone

Molindone or NGI-221 (3-ethyl-6,7-dihydro-2-methyl-5-(morpholinomethyl)indol-4-(5H)-one) is a dihydroindolone neuroleptic which is structurally distinct from the other 15 classes of neuroleptics, and has the following structure:

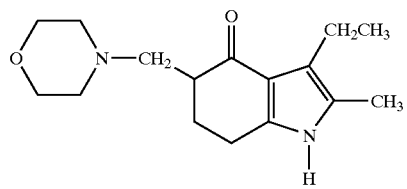

The compound can be prepared in its racemic form or as an enantiomer, e.g. as the levorotatory enantiomer. Molindone can be prepared according to the procedures described in U.S. Pat. No. 3,491,093 and U.S. Pat. No. 4,065,453.

Derivatives of molindone which are dihydroindolones may also be administered according to the present invention for the treatment of oppositional defiant disorder and/or conduct disorder. Derivatives that are acceptable are given by the following formula (II)

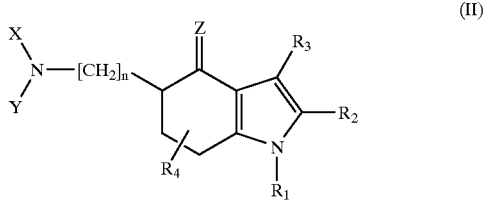

(II)

In this formula n is 1, 2 or 3.

$R_1$, $R_2$, $R_3$ and $R_4$ are each independently a hydrogen atom, an optionally substituted alkyl, an optionally substituted alkenyl or an optionally substituted alkynyl radical (the optional substituent of the alkyl, alkenyl or alkynyl radical being 1–3 radicals of amino, alkylamino, dialkylamino, alkanoylamino, alkoxycarbonylamino or alkylsulfonylamino); a hydroxy group, an alkoxy group, an alkylthio group, an alkylsulfinyl group, a lower alkylsulfonyl group, a halogen atom, a carboxyl group, a lower alkoxy-carbonyl group, a benzyloxycarbonyl group, a cyano group, a benzyloxy group, a lower alkanoyloxy group, a cycloalkyl group, a cycloalkyl group, an aryl group, an aralkyl group, a substituted aryl group, a heteroaryl group, a substituted heteroaryl group, a benzenesulfonyloxy group being optionally substituted by an alkyl group; a lower alkanoylamino group, a lower alkoxycarbonylamino group, a lower alkylsulfonamido group or a phthalimido group.

In addition $R_3$ can also be one or more members selected from the group consisting of hydrogen, amino, alkylamino, dialkylamino, alkanoylamino, alkoxycarbonylamino, and alkylsulfonylamido.

In a preferred embodiment $R_1$ designates hydrogen, a $C_{1-4}$ alkyl, benzyl, phenyl or 2-, 3- or 4-pyridyl. More preferably $R_1$ is hydrogen or a lower alkyl.

Preferably $R_2$ and $R_3$ are each independently alkyl, alkenyl, cycloalkyl, phenyl, halogeno-phenyl or lower alkoxy phenyl. Preferably $R_2$ and $R_3$ are each independently alkyl, more preferably lower alkyl.

Preferably $R_4$ designates hydrogen or a lower alkyl and is attached to carbon atom 6 or 7 of the indole nucleus. Preferably $R_4$ is hydrogen.

X and Y designate lower alkyl, hydroxy lower alkyl, lower acyloxy alkyl, carbamoyloxy lower alkyl and phenyl lower alkyl. Alternatively X and Y may be linked together and then constitute, together with the nitrogen atom to which they are attached, an NXY moiety that is an optionally substituted heterocyclic ring. In one preferred embodiment X and Y are a lower alkyl or phenyl lower alkyl. In a second preferred embodiment X and Y are linked together and then constitute, together with the nitrogen atom to which they are attached, an NXY moiety that is a heterocyclic ring. Preferably in this embodiment NXY is a morpholinyl group, a pyrrolidyl group, imidazolidinyl group, a piperidyl group or a piperazinyl group, each of which can be substituted; more preferably NXY is a morpholinyl group, a piperidyl group or a piperazinyl group, each of which can be substituted (e.g. by a lower alkyl group, a lower alkoxy group or a phenyl group optionally substituted with a hydroxy group or a lower alkyl group or a lower alkoxy group).

Z is selected from the group consisting of oxo, thio, seleno, telluro, and NH. Preferably Z is oxo.

Pharmaceutically acceptable acid addition salts of molindone or of said compound (II) can also be employed. Such derivatives, especially those with longer-lasting effects than molindone, will be especially useful in treating persons with ODD.

Throughout the description of the present invention the following definitions are employed unless stated otherwise.

The term "alkyl group" includes, for example, a straight chain or branched chain alkyl group having 1 to 15 carbon atoms, such as methyl, ethyl, propyl, 2-propyl, butyl, 2-butyl, 2-methylpropyl, 1,1-dimethylethyl, pentyl, 3-pentyl, 3-methylbutyl, hexyl, heptyl, octyl, undecyl, dodecyl, hexadecyl, 2,2-dimethyl-dodecyl, 2-tetradecyl, n-octadecyl, 3-hexyl, 4-methyl-pentyl, 4-heptyl, octyl, 4-octyl, decyl, etc. Preferably the alkyl group has 1 to 10, more preferably 1 to 4 carbon atoms. "Lower alkyl" is used to denote a straight chain or branched chain alkyl group having 1 to 4 carbon atoms.

In the alkanoyl group and the alkoxy group the contained alkyl group or lower alkyl group is as defined above. In the acyl group the contained alkyl group, lower alkyl group or aryl group is as defined above.

The expression "alkenyl group" includes, for example, a straight chain or branched chain alkenyl group having 2 to 20 carbon atoms and having 1 to 2 double bonds, such as vinyl, allyl, 2-propenyl, 2-butenyl, 3-methyl-2-butenyl, 3-pentenyl, 2-octenyl, 5-nonenyl, 4-undecenyl, 5-heptadecenyl, 3-octadecenyl, 9-octadecenyl, 2,2-dimethyl-9-octadecenyl, 9,12-octadecadienyl, 2-methyl-2-propenyl, 3-butenyl, 4-pentenyl, 3-hexenyl, 3-ethyl-2-pentenyl, 4-ethyl-3-hexenyl, etc. Preferably the alkenyl group has 2 to 10, more preferably 2 to 4 carbon atoms.

"Alkynyl group" includes, for example, a straight chain or branched chain alkynyl group having 2 to 20 carbon atoms, such as 2-propynyl, 3-butynyl, 4-pentynyl, 3-hexynyl, 5-methyl-2-hexynyl, 6-methyl-4-heptynyl, or any of the above alkenyl groups wherein the double bond has a triple bond, etc. Preferably the alkynyl group has 2 to 10, more preferably 2 to 4 carbon atoms.

The term "cycloalkyl group" includes, for example, a cycloalkyl group having 3 to 8 carbon atoms, such as cyclopropyl, cyclobutyl, cyclopentyl, cyclohexyl, cycloheptyl, cyclooctyl, etc. Preferably the cycloalkyl group includes cyclopentyl, cyclohexyl and cycloheptyl.

The aromatic group includes, for example, an aryl group and a heteroaryl group.

"Aryl group" includes groups having one or more aromatic rings and from 5 to 20 carbon atoms. Examples typically include one or more phenyl rings.

The term "heteroaryl group" includes, for example, a 5- to 6-membered heteromonocyclic group having 1 or 2 nitrogen atoms, a 5- to 6-membered heteromonocyclic group having 1 or 2 nitrogen atoms and one oxygen atom or one sulfur atom, a 5-membered heteromonocyclic group having one oxygen atom or one sulfur atom, a heterobicyclic group formed by fusing a 6-membered ring and a 5- or 6-membered ring and having 1 to 4 nitrogen atoms, such as 2-pyridyl, 3-pyridyl, 4-pyridyl, 2-thienyl, 3-thienyl, 3-oxadiazolyl, 1-imidazolyl, 2-imidazolyl, 2-thiazolyl, 3-isothiazolyl, 2-oxazolyl, 3-isoxazolyl, 2-furyl, 3-furyl, 3-pyrrolyl, 2-quinolyl, 8-quinolyl, 2-quinazolinyl, 8-purinyl, etc.

The term "heterocyclic group" includes, for example, a 5- to 8-membered (preferably 5- or 6-membered) heteromonocyclic group having one or two heteroatoms selected from N, O and S. The heterocyclic group can be saturated or unsaturated and can be substituted or unsubstituted.

Examples of the heterocyclic group are those listed above for the heteroaryl group and morpholinyl, pyrrolidyl, pyrrolinyl, imidazolidinyl, imidazolinyl, pyrazolidinyl, pyrazolinyl, piperidyl and piperazinyl. Preferred heterocyclic groups are morpholinyl, pyrrolidyl, imidazolidinyl, piperidyl and piperazinyl. Particularly preferred are morpholinyl, piperidyl and piperazinyl.

The substituted aryl, heteroaryl or heterocyclic group has one or more substituents which are the same or different, and the substituents are, for example, a halogen atom, a cyano group, a trifluoromethyl group, a nitro group, a hydroxy group, a methylenedioxy group, a lower alkyl group, a lower alkoxy group, a benzyloxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkyl-sulfonyl group, a lower alkanoylamino group, a lower alkylsulfonamido group, or a group of the formula: $-M_1$-E-Q ($M_1$ is a direct bond, an oxygen atom, a sulfur atom, or a group of the formula: $-NR_5-$ ($R_5$ is a hydrogen atom or a lower alkyl group), E is a divalent aliphatic hydrocarbon group having 1 to 15 (preferably 1 to 4) carbon atoms and optionally containing an unsaturated bond, or a phenylene group, Q is a hydrogen atom, a hydroxy group, a carboxyl group, a lower alkoxycarbonyl group, a benzyloxycarbonyl group, a halogen atom, a cyano group, a benzyloxy group, a lower alkoxy group, a lower alkanoyloxy group, a lower alkylthio group, a lower alkylsulfinyl group, a lower alkyl-sulfonyl group, a benzenesulfonyloxy group being optionally substituted by an alkyl group, a lower alkanoylamino group, a lower alkoxycarbonylamino group, a lower alkylsulfonamido group, a phthalimido group, a cycloalkyl group, an aryl group, a heteroaryl group, a group of the formula: $-NR^4R^6$ ($R^4$ and $R^6$ are independently a hydrogen atom, a lower alkyl group, a di-lower alkylamino-substituted lower alkyl group, a lower alkoxy-substituted lower alkyl group, a cycloalkyl group, a lower alkoxycarbonyl group, a heteroarylmethyl group, or an aralkyl group, or $R^4$ and $R^6$ may combine each other together with the nitrogen atom to which they bond, and form a saturated cyclic amino group having 4 to 8 carbon atoms as ones forming the ring, and optionally having one $-NR^{20}$ wherein $R^{20}$ is a hydrogen atom, a lower alkyl group, a phenyl group, a lower alkoxycarbonyl group, or a benzyl group or one oxygen atom in the cycle thereof; or a group of the formula: $-C=O$, $NR^4R^6$ ($R^4$ and $R^6$ are as defined above)). The choice of the substituents will depend on the particular compound and the desired activity. Preferred substituents include a halogen atom, a trifluoromethyl group, a hydroxy group, a lower alkyl group, a lower alkoxy group, a phenyl group or a phenyl group substituted with a hydroxy group, a lower alkyl group or a lower alkoxy group.

The term "aralkyl group" includes groups consisting of an aryl group or substituted aryl group bonded to a lower alkyl group.

Owen and Cole (1989) reviewed the laboratory and clinical findings of studies of molindone and found the following: 1) it exhibits many similarities to other neuroleptics, including dopamine receptor blockade, antipsychotic efficacy and extrapyramidal side effects; 2) it has atypical properties and inhibits the enzyme monoamine oxidase in vitro and in vivo; 3) it causes less dopamine receptor supersensitivity than other neuroleptics and thus may be less likely to cause tardive dyskinesia; 4) it appears to have a greater effect on mesolimbic and mesocortical dopamine neurons than on those in the nigrostriatal dopamine system; and 5) clinically it has a tendency to cause weight loss and may have less effect on seizure threshold than conventional antipsychotic agents.

The pharmacology of molindone in humans has been studied and reported in several articles and summarized in Owen and Cole (1989) as set out in the following. Absorption of molindone is rapid after both oral and intramuscular administration, with maximal serum concentration occurring at approximately 1.1 and 0.6 hours, respectively (Owen and Cole, 1989; Zetin et al., 1985; Fann and Moreira, 1985). Molindone is less lipophilic than other neuroleptic agents and approximately 24% of molindone in plasma is not bound to protein, compared with 9% for haloperidol and 0.13% for chlorpromazine (Owen and Cole, 1989; Freedberg et al., 1979). Accordingly, the elimination half-life of molindone is approximately 2 hours, which is much shorter than the half-lives of traditional antipsychotic agents (Zetin et al., 1985; Wolf et al., 1985; Claghom, 1985). Even at steady state doses of 50 mg twice per day or 100–150 mg in a single daily dose, molindone concentrations are negligible at 12 hours after the last dose (Wolf et al., 1985; Zetin et al., 1985). Concomitant lithium therapy prolongs the half-life of molindone 5 at least fourfold (Wolf and Mosnaim, 1986).

Despite its short plasma half-life, the clinical duration of action of a therapeutic dose of molindone is at least 24 hours (Ayd, 1974). This has been attributed to the activity of molindone being mediated by an active metabolite (Koe, 1979; Meller and Friedman, 1982; Balsara et al., 1984; Wolf et al., 1985; Greengard, 1975). Molindone has been used to treat several illnesses. Owen and Cole (1989) summarize these studies. They state that more than 20 studies of the antipsychotic efficacy of molindone were performed in schizophrenic patients, with most studies showing minimal to moderate improvement in a majority of patients. In these studies, 2 mg of molindone appeared to be equivalent to 1 mg of trifluoperazine with respect to both antipsychotic efficacy and side effects (Owen and Cole, 1989). Intramuscular molindone has been shown to be as effective as intramuscular haloperidol in the treatment of acutely psychotic or agitated patients (Owen and Cole, 1989; Binder et al., 1981; Smythies et al., 1982; Escobar et al., 1985). Owen and Cole (1989) also summarize studies testing the use of molindone to treat anxiety and depression. They cite two pilot studies which suggested that molindone may have some antianxiety effects although the differences between molindone and placebo did not reach statistical significance (Case et al., 1970; Keliner et al., 1972). Molinone at a dosage of as little as 3 mg/day showed antianxiety effects in patients suffering from premenstrual tension (Shader and Harmatz, 1975). Two studies are cited by Owen and Cole (1989) relating to the use of molindone as an antidepressant. In a placebo-controlled trial using low-dose molindone (mean dose 14.5 mg/day), the patient showed some improvement in both anxiety and depression ratings, although the changes were not statistically significant (Goldstein and Brauzer, 1971). Molindone (10–30 mg/day) was compared with tranylcypromine in a single-blind parallel study of 19 patients with refractory depression and in which the patients had not responded to or had not tolerated tricyclic antidepressant agents (Small et al., 1981). Five of the 10 patients treated with molindone were described as showing definite improvement whereas only two of the tranylcypromine-treated patients were described as being definitely better (Small et al., 1981).

Studies have been performed with molindone being used to treat children and geriatric patients. Owen and Cole (1989) cite 3 studies involving children. These are a small pilot study showing molindone to be effective in treating schizophrenic children, ages 3–5 years (Campbell et al., 1971), an open trial with six patients (ages 6–11 years) diagnosed as having undersocialized conduct disorder, aggressive type, who showed some improvement in aggressive behavior and in the Nurses' Global Assessment Scale (Greenhill et al., 1981), and a double-blind study comparing molindone with thioridazine in 31 children (ages 6–11 years) with undersocialized conduct disorder, aggressive type, this study reporting improvement in behavior ratings with both drugs and no significant differences in effectiveness between the drugs (Greenhill et al., 1985).

Molindone was shown to be both effective and well-tolerated in a sample of geriatric patients with a variety of psychiatric disorders, including dementia (Peper, 1985), with an average daily dose in the last week of the study of 100 mg, which is comparable to doses used in young adults (Owen and Cole, 1989).

Owen and Cole (1989) report just six published cases of tardive dyskinesia associated with molindone treatment (Camp, 1977; Ananth and Carrillo, 1983; Cole et al., 1987). In these cases, although the movement disorder emerged during treatment with molindone, each patient had received at least one other antipsychotic agent at some time prior to receiving molindone (Owen and Cole, 1989). Thus, no case of tardive dyskinesia had been reported (as of 1989) in which molindone was the only possible causative agent (Owen and Cole, 1989). Molindone is associated with side effects similar to other antipsychotic agents. Owen and Cole (1989) report that extrapyramidal side effects have been reported in every study and include rigidity, tremor, and akathisia. Drowsiness was reported as a common side effect (Sugerman and Herrmann, 1967; Krumholz et al., 1970; Abuzzahab, 1973), while dry mouth (Sugerman and Herrmann, 1967; Abuzzahab, 1973), blurred vision (Shelton et al., 1968; Abuzzahab, 1973), and orthostatic hypotension (Shelton et al., 1968; Turek et al., 1970) appeared to be much less frequent. One side effect unique to molindone appears to be significant weight loss (Krumholz et al., 1970; Gallant et al., 1973; Freeman and Frederick, 1969; Clark et al., 1970; Escobar et al., 1985; Gardos and Cole, 1977), although one study found no difference between molindone and other neuroleptics and suggested that higher doses of molindone may cause weight gain (Parent et al., 1986).

Owen and Cole (1989) cite a few studies which reported mild to moderate euphoria in some patients taking molindone although the number of affected patients was small.

Formulations Comprising the Active Ingredient

The indole compounds used in the present invention can be formulated into compositions comprising the compound together with a pharmaceutically suitable carrier. The carrier can be either a solid or liquid and the compositions can be in the form of tablets, liquid-filled capsules, dry-filled capsules, aqueous solutions, non-aqueous solutions, injectables, suppositories, syrups, suspensions and the like. The compositions can contain suitable preservatives and coloring and flavoring agents. Some examples of the carriers which can be used in the preparation of the products are gelatin capsules; sugars, such as lactose and sucrose; starches; dextrans; cellulosics, such as methyl cellulose, cellulose acetate phthalate; gelatin; talc; steric acid salts; vegetable oils, such as peanut oil, cottonseed oil, sesame oil, olive oil, corn oil, and oil of theobroma; liquid petrolateum; polyethylene glycol; glycerin; sorbitol; propylene glycol; ethanol; sodium metabisulfite, disodium ethylenediaminetetraacetic acid; agar; water; and isotonic saline.

In formulating the compounds, conventional practices and precautions are used. The composition intended for parenteral administration must be sterile either by using sterile ingredients and carrying out the production under aseptic conditions or by sterilizing the final composition by one of the usual procedures such as autoclaving under appropriate temperature and pressure conditions. Customary care should be exercised so that no incompatible conditions exist between the active components and the diluent preservative or flavoring agent, or in the conditions employed in preparation of the compositions.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric-coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA (ethylenediaminetetraacetic acid). In addition, parenteral solutions can contain preservatives, such as benzalkonium chloride, methyl- or propyl-paraben, and chlorobutanol.

The compounds of formula I or II, including molindone, can be prepared and administered in the form of a pharmaceutically acceptable salt, preferably an acid addition salt. It will be understood by the skilled reader that the compound used in the present invention is capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

The compound used in this invention is an amine, and accordingly reacts with any of a number of inorganic and organic acids to form pharmaceutically acceptable acid addition salts. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, b-hydroxybutyrate, glycollate, tartrate, methanesulfonate, propanesulfonate, naphthalene-1-sulfonate, naphthalene-2-sulfonate, mandelate, various carbonates and the like. Preferred pharmaceutically acceptable salts are those formed with hydrochloric acid.

Suppositories contain the active ingredient in a suitable oleaginous or water-soluble base. The oleaginous class includes cocoa butter and fats with similar properties: the water-soluble class includes polyethylene glycols. Suitable pharmaceutical carriers are described in Remington's Pharmaceutical Sciences, E. W. Martin, a standard reference text in this field.

The compound used in the invention or its salt can be administered as treatment by any means that produces contact of the active agent with the agent's site of action in the body. The compounds can be administered orally, parenterally, percutaneously, intravenously, intramuscularly, intranasally or rectally. It can be administered formulated as a cream or in a patch which slowly delivers the drug in a time-release fashion. Because the compounds, including molindone, are short-acting drugs, it is preferred that it be administered in a long-acting form such as in a time-release capsule, a patch or sustained release formulations. Preferably the compositions are in unit dosage forms such as tablets, pills, capsules, powders, granules, solutions, suspensions, or suppositories, and are formulated for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of the compound, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient. The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The dosage administered will vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

When administering the compounds, it is preferred that a low dosage is first administered and that the dosage is raised until an effect is seen. In this manner, the lowest effective dose can be used which will avoid or minimize any side effects. Although the reverse procedure of beginning a patient at a high dosage and lowering the dosage until side effects disappear or are minimized can also be used, it has been seen that after once experiencing side effects the patients are less likely to take the medication. Therefore the method of beginning a patient at a low dosage and increasing it until an effective dosage is reached is preferable to beginning at a high dosage and then lowering the dosage.

Typically the effective dose in a human patient is 50–150 mg/day, preferably 1.25 to 10 mg every four hours, especially 5–10 mg every four hours.

Test on the use of Molindone to Treat Patients with Oppositional Defiant Disorder and Conduct Disorder It has now been found that oppositional defiant disorder and conduct disorder can be effectively treated by the administration of molindone. More than 50 patients with ODD have been successfully treated with molindone with the usual therapeutic dose to be 1.25 to 10 mg every 4 hours. A number of recently marketed atypical antipsychotics such as risperidone (Risperdal) and olanzapine (Zyprexia) are also capable of effectively treating ODD (unpublished observations). However, unlike molindone, these drugs also antagonize serotonin 2 receptors. Their combination of a higher level of antagonism of dopamine receptors than molindone and antagonism of serotonin 2C receptors, makes them act like "anti-phen-fen" the recently discontinued pair of diet medications. As such these two drugs are associated, especially in children, with an unacceptable level of weight gain, sometimes approaching a pound a day. The side effect is totally unacceptable to teenagers. Molindone rarely, if ever, causes weight gain. One side effect unique to molindone appears to be significant weight loss (Krumholz et al., 1970; Gallant et al., 1973; Freeman and Frederick, 1969; Clark et al., 1970; Escobar et. al., 1985; Gardos and Cole, 1977), although one study found no difference between molindone and other neuroleptics and suggested that higher doses of molindone may cause weight gain (Parent et al., 1986).

Case histories are set out in the following examples, which are offered by way of illustration and are not intended to limit the invention in any manner.

EXAMPLES

Example 1

Patient A. H. is a 10 year old adopted male diagnosed with attention deficit hyperactivity disorder (ADHD), Tourette syndrome and oppositional defiant disorder. In early grade school he was very hyperactive and could not sit still. He was placed in special education classes from first grade on.

Because of rage episodes he was suspended multiple times. Motor tics consisting of facial grimacing, crotch touching, and a complex leg tic and vocal tics consisting of spitting and sniffing along with swearing started at age three. Other features included obsessive compulsive behavior, stuttering, and learning disorders. He was diagnosed as having ADHD at 3½ years of age. Treatment with methylphenidate, dextroamphetamine, and pemoline were all unsuccessful. Treatment with clonidine 0.05 mg three times per day (tid) improved both the tics and the ADHD. By 7 years of age he was having daily rage episodes in the home after school. He was extremely competitive, oppositional and defiant. Although the tics, ADHD, and some of the behavioral problems improved following treatment with clonidine and sertraline the rage episodes, tantrums, and hitting of his siblings and parents continued. Treatment was started with very small doses of molindone, ¼ of a 5 mg tablet every 4 hours. This resulted in the immediate cessation of the tantrums, hitting and rages and less swearing. After three months the dose was raised to ½ of a 5 mg tablet every 4 hours which was found to be more effective and continued to be effective with continued treatment.

Example2

Patient E. S. is a 6 year old male diagnosed with ADHD, ODD and CD. Beginning at 5 years of age in kindergarten he was very hyperactive and had a very short attention span. He also began to violently attack other children. He kicked one boy in the face and once vandalized the school. He was kicked out of after school day care because of attacking other children. He was even worse at home with rage attacks and tantrums occurring at least twice a day. These were set off by trivial things. Although the ADHD symptoms improved following treatment with methylphenidate, 10 mg tid, the rage episodes, tantrum and violent behaviors persisted. Following treatment with molindone, 2.5 mg every 4 hours, the tantrums and aggressive behaviors disappeared. It was still effective after 6 months of use.

Example 3

Patient J. K. is a 14 year old male. He began to have constant vocal tics at age 3. Motor tics started at age 4, consisting of licking his lips, rolling his eyes, hand and foot tics. In preschool he was constantly fighting and confronting others. At 6 years of age a diagnosis of ADHD was made and he was treated with methylphenidate with some improvement in attention span but little effect on the aggressive and oppositional behavior. He was still hitting and slapping other children. When first seen at age 8, the major presenting symptom was his aggressive and oppositional behavior. Additional diagnoses were ODD and CD. The parents were divorced. The father had a history of drug and alcohol addiction and chronic motor tics. His father was an alcoholic. The mother was asymptomatic but had a brother with drug and alcohol addiction. By 10 years of age, despite treatment with methylphenidate 20 mg twice a day (bid), haloperidol 0.5 mg and paroxitine 10 mg, he was talking non-stop, lying, hitting things and people, and extremely oppositional. Treatment with molindone 10 mg bid brought about a dramatic decrease in oppositional behavior. Later, the molindone was discontinued and risperidone or olanzapine was used instead. While they also produced a significant improvement in the oppositional behavior, both resulted in significant weight gain. When they were discontinued, the argumentative, rude, oppositional and abusive behavior returned. Molindone was again initiated and resulted in immediate and dramatic improvement in the behavior.

Example 4

The in vitro activity of Molindone and two derivatives thereof on cells expressing dopamine and serotonine receptors was investigated. The formulae of the compounds are

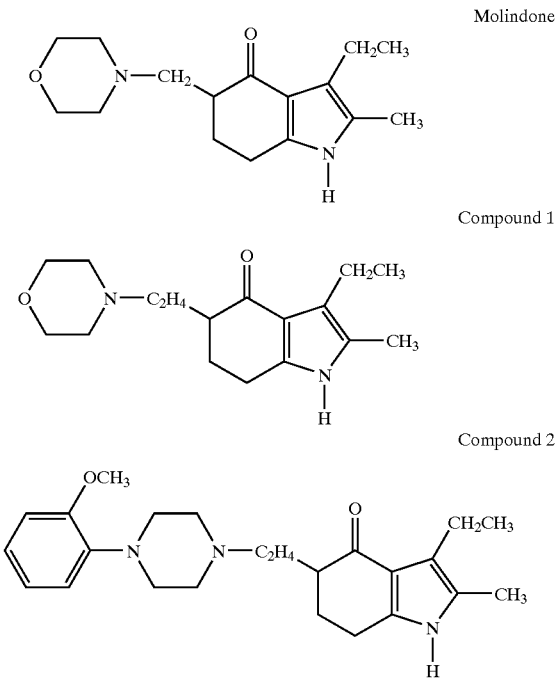

TABLE 1

| | pK$_i$ | | | pK$_i$ ratio | pA$_2$ |
|---|---|---|---|---|---|
| Compound | D$_1$ | D$_2$ | 5-HT$_{2A}$ | 5-HT$_{2A}$/D$_2$ | 5-HT$_{2A}$ |
| Molindone | 5.80 | 7.48 | 5.85 | 0.78 | 6.18 |
| Compound 1 | 5.67 | 6.23 | 6.04 | 0.97 | 6.98 |
| Compound 2 | — | 7.55 | 7.04 | 0.97 | 7.50 |

Table 1 shows the in vitro activity of Molindone and derivative compounds 1 and 2. Here, the pKi value is a measure for the binding affinity of the test compounds to the receptors present in cell membrane homogenates. D1 refers to the Dopamine 1 receptor, D2 refers to the Dopamine 2 receptor, and 5-HT2A refers to the Serotonin 2A receptor, while the pKi ratio presents the ratio of Serotonin 2A binding to Dopamine 2 binding.

Compounds 1 and 2 have in vitro Dopamine 2 and Serotonin 2A receptor binding activity profiles similar to that of Molindone. Compound 1 is also similar to the in vitro Dopamine 1 receptor binding profile of Molindone. These similar activities indicate that that these compounds will also prove effective in treatment of ODD and CD.

All of the references, publications and patents referred to herein are hereby incorporated by reference.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

List of References

Abuzzahab F S (1973). *J. Gun. Pharmacol.* fl: 226–233.
Achenbach T M (1991). *Manual for the Child Behavior Checklist/4-18 and 1991 Profile.* Burlington, University of Vermont, Department of Psychiatry.
Achenbach T M and Edeibrock C S (1986). *Manual for the Teacher's Report Form and Teacher Version of the Child Behavior Profile.* Burlington, University of Vermont, Department of Psychiatry.
American Psychiatric Association (1987). *Diagnostic and Statistical Manual of Mental Disorders*, Third Edition, revised (DSM-III-R).
American Psychiatric Association (1994). *Diagnostic and Statistical Manual of Mental Disorders*, Fourth Edition (DSM-IV). Washington, D.C.
Ananth J and Carrillo R (1983). *J. Clin. Psychiatry* 44:276.
Anderson J C, et al. (1987). *Arch. Gen. Psychiatry* 44:69–76.
Ayd F J (1974). *Dis. Nerv. Sys.* 3:447–452.
Balsara J J, et al. (1984). *J. Pharm. Pharmacol.* 3.~:608–613.
Barkley R A, et al. (1991). *J. Child Psychol. Psychiatry* 3.2:233–255.
Bhatia S C, et al. (1985). *Drug Intell. Clin. Pharm.* 1.2:744–746.
Biederman J, et al. (1996). *J. Am. Acad. Child Adolesc. Psychiatry* 3.5:1193–1204.
Binder R, et al. (1981). *J. Clin. Psychiatry* 42:203–206.
Bird H R, et al. (1988). *Arch. Gen. Psychiatry* 4.5:1120–1126.
Camp E W (1977). *Dis. Nerv. Sys.* 3.~:759.
Campbell M, et al. (1971). *Curr. Ther. Res.* fl:28–33.
Cantwell D P and Baker L (1989). *J. Am. Acad. Child Adolesc. Psychiatry* Za:691–700.
Caron C and Rutter M (1991). *J Child Psychol. Psychiatry* 32:1063–1080.
Case W G, et al. (1970). *Curr. Ther. Res.* 12:136–141.
Claghom J L (1985). *J. Clin. Psychiatry* 46(8. suppl.):30–33.
Clark M L, et al. (1970). *Clin. Pharmacol. Ther.* fl:680–688.
Cohen P, et al. (1987). *J. Am. Acad Child Adolesc. Psychiatry* 2.□:63 1–63 8.
Cohen P, et al. (1991). *J. Am. Acad Child Adolesc. Psychiatry* 3.Q:989–993.
Cohn L D (1991). *Psychol. Bull.* 1Q2:252–266.
Cole J O et al. (1987). In: Casey D E, Dardos G, eds. *Tardive dyskinesia and neuroleptics: from dogma to reason.* Washington D.C.: American Psychiatric Press, pp. 33–54.
Escobar J I, et al. (1985). *J. Gun. Psychiatry* 46(8. suppL): 15–19.
Fann W E and Moreira A F (1985). *J. Clin. Pharmacol.* 25:305–306.
Freedberg K A, et al. (1979). *Life Sd.* 24:2467–2473.
Freeman H and Frederick AND (1969). *Curr. Ther. Res.* 11:670–676.
Gallant D M, et al. (1973). *Curr. Ther. Res.* 15:915–918.
Gardos G and Cole J O (1977). *Am. J. Psychiatry* 13.4:302–304.
Glickman L (1987). *J. Gun. Psychiatry* 4a:299–300.
Goldstein B J and Brauzer B (1971). *Curr. Ther. Res.* j3.:344–349.
Gomez E A (1985). *Tex. Med. J.* 47–48.
Goodenough F L (1931). *Anger in Young Children.* Minneapolis, University of Minnesota Press.
Greengard P (1975). In: Almgren O, Carlsson A, Engel J, eds. *Chemical tools in catecholamine research II.* Amsterdam: North Holland Publishing, pp. 249–256.
Greenhill L L, et al. (1981). *Psychopharmacol. Bull.* fl:125–127.
Greenhill, L L, et al. (1985). *J. Gun. Psychiatry* 46(8. suppl.):26–29.
Johnson S B, et al. (1986). *J. Clin. Psychiatry* 42:607–608.
Kashani J H, et al. (1987). *Am. J. Psychiatry.* 14.4:584–589, correction, j.44:1114.
Kazdin A E (1987). *Psychol Bull.* 0.1.Q2:187–203.
Keilner R, et al. (1972). *J. Clin. Pharmacol.* 12:472–476.
Koe B K (1979). In Usdin E, Kopin I J, Barchas J, eds. *Catecholamines: basic and clinical frontiers. Proceedings of the Fourth International Catecholamine Symposium.* New York: Pergamon Press, pp. 740–742.
Krumholz W V, et al. (1970). *Curr. Ther. Res.* 12:94–96.
Lahey B B, et al. (1992). *J. Am. Acad Child Adolesc. Psychiatry* 3.1:539–546.
Loeber R (1991). *Hospital and Community Psychiatry* 42:1099–1102.
Loeber R, et al. (1991). *J. Abnorm. Psychol.* 0.1~.Q:379–390.
Looney J G and Oldham D G (1989). In *Comprehensive Textbook of Psychiatry*, 5th ed., vol. 2. Edited by Kaplan H I, Sadock B J. Baltimore, Williams & Wilkins.
McGee R, et al. (1990). *J. Am. Acad. Child Adolesc. Psychiatry* 22:611–619.
Meller E and Friedman E (1982). *J Pharmacol. Exp. Ther.* 22.Q:609–615.
Owen R R and Cole J O (1989). *Journal of Clinical Psychopharmacology* 2:268–276.
Pandurangi A K and Narasimhachari N (1988). *J. Clin. Psychiatry* 42:37–38.
Parent M M, et al. (1986). *Drug Intell. Clin. Pharm.* 2~:873–875.
Pelham W E, et al. (1992). *J. Am. Acad. Child Adolesc. Psychiatry* 3.1:210–218.
Peper M (1985). *J. Clin. Psychiatry* 46(8. suppl.):26–29.
Quay H C (1986). In *Psychopathological Disorders of Childhood*, 3rd ed. Edited by Quay H C, Werry J S. New York, John Wiley & Sons.
Ramsay R A, et al. (1970). *J. Clin. Pharmacol.* 3:46–48.
Rey J M (1993). *Am. J. Psychiatry* ISQ: 1769–1778.
Robins L N, et al. (1991). In *Psychiatric Disorders in America.* Edited by Robins L N, Regier D A. New York, Free Press.
Rutter M (1988). In Assessment and Diagnosis in Child Psychopathology, Rutter M et al., eds. London, David Fulton.
Rutter M and Oilier H (1983). *Juvenile Delinquency.* Middlesex, England, Penguin.
Rutter M and Shatter D (1980). *J. Am. Acad. Child Psychiatry* 12:371–394.
Shader R I and Harmatz I S (1975). *Curr. Ther. Res.* 12:403–406. Shelton J, et al. (1968). *J. Clin. Pharmacol.* ~:190–195.
Shepherd M, et al. (eds.) (1971). *Childhood Behaviorand Mental Health.* London, University of London Press.
Simpson G M and Krakov L (1968). *Curr. Ther. Res.* 1:41–46.
Small J O, et al. (1981). *J. Clin. Pharmacol.* 21:351–358.
Smythies J R, et al. (1982). *Curr. Ther. Res.* 32:752–756.
Spitzer R L, et al. (1990). *J. Am. Acad. Child Adolesc. Psychiatry* 22:690–697.
Sugerman A A and Herrmann J. (1967). *Clin. Pharmacol. Ther.* ~:261–265.
Turek I S, et al. (1970). *J. Clin. Pharmacol.* j.Q:349–355.
Werry J S, et al. (1983). In *International Perspectives on DSM-III*, Spitzer R L et al., eds. Washington, D.C., American Psychiatric Press.
Werry I S, et al. (1987). *J. Am. Acad. Child Adolesc. Psychiatry* 2~:133–143. Wolf M E, et al. (1985). *Res.*

Commun. Psychol. Psychiatry Behav. IQ:215–220. Wolf M E and Mosnaim A D (1986). Res. Commun. Psychol. Psychiatry Behav. 11:23–28.

World Health Organization: The ICD-10 Classification of Mental and Behavioral Disorders: Clinical Descriptions and Diagnostic Guidelines. Geneva, WHO, 1992.

World Health Organization: Diagnostic criteria for research, mental and behavioral disorders, in ICD-10: May 1990 Draft for Field Trials. Geneva, WHO, 1990.

Zetin M, et al. (1985). Gun. Ther. 2:169–175.

U.S. Patents
U.S. Pat. No. 3,491,093
U.S. Pat. No. 3,636,042
U.S. Pat. No. 4,065,453
U.S. Pat. No. 4,148,896

What is claimed is:

1. A method of treating oppositional defiant disorder in a patient diagnosed therewith wherein said method comprises administering a therapeutically effective amount of indole compound I, represented by general formula I,

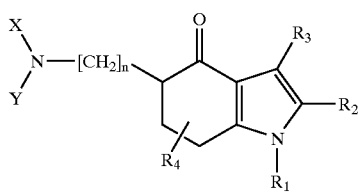

(I)

or the indole compound I as a pharmaceutically acceptable acid addition salt of the compound of general formula I to said patient, wherein:

n is 2 or 3;

$R_1$ designates hydrogen, a lower alkyl, benzyl, phenyl or 2-, 3- or 4-pyridyl;

$R_2$ and $R_3$ are each independently alkyl, alkenyl, cycloalkyl, phenyl, halogeno-phenyl or lower alkoxy phenyl;

$R_4$ designates hydrogen or a lower alkyl and is attached to carbon atom 6 or 7 of the indole nucleus; and X and Y designate lower alkyl, hydroxy lower alkyl, lower acyloxy alkyl, carbamoyloxy lower alkyl and phenyl lower alkyl or alternatively X and Y may be linked together and then constitute, together with the nitrogen atom to which they are attached, an NXY moiety that is an optionally substituted heterocyclic ring.

2. A method of treating oppositional defiant disorder in a patient diagnosed therewith wherein said method comprises administering a therapeutically effective amount of indole compound II, represented by general formula II,

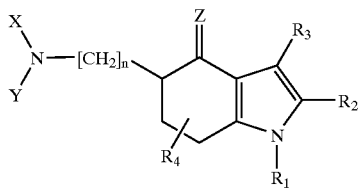

(II)

or the indole compound II as a pharmaceutically acceptable acid addition salt of the compound of general formula II, to said patient, wherein:

n is 2 or 3;

$R_1$, $R_2$, $R_3$ and $R_4$ are each independently a hydrogen atom, an optionally substituted alkyl, an optionally substituted alkenyl or an optionally substituted alkynyl radical (the optional substituent of the alkyl, alkenyl or alkynyl radical being 1–3 radicals of amino, alkylamino, dialkylamino, alkanoylamino, alkoxycarbonylamino or alkylsulfonylamino); a hydroxy group, an alkoxy group, an alkylthio group, an alkylsulfinyl group, a lower alkylsulfonyl group, a halogen atom, a carboxyl group, a lower alkoxy-carbonyl group, a benzyloxycarbonyl group, a cyano group, a benzyloxy group, a lower alkanoyloxy group, a cycloalkyl group, a cycloalkyl group, an aryl group, an aralkyl group, a substituted aryl group, a heteroaryl group, a substituted heteroaryl group, a benzenesulfonyloxy group being optionally substituted by an alkyl group; a lower alkanoylamino group, a lower alkoxycarbonylamino group, a lower alkylsulfonamido group or a phthalimido group;

or $R_3$ is also one or more members selected from the group consisting of hydrogen, amino, alkylamino, dialkylamino, alkanoylamino, alkoxycarbonylamino, and alkylsulfonylamido;

X and Y designate lower alkyl, hydroxy lower alkyl, lower acyloxy alkyl, carbamoyloxy lower alkyl and phenyl lower alkyl, or X and Y may be linked together and then constitute, together with the nitrogen atom to which they are attached, an NXY moiety that is an optionally substituted heterocyclic ring; and Z is selected from the group consisting of oxo, thio, seleno, telluro, and NH.

3. The method of claim 1 wherein said n is 2 and said NXY moiety is morpholine.

4. The method of claim 1, wherein said n is 2 and said NXY moiety is N-(2-methyoxyphenyl)piperazine.

5. The method of claim 1 or 2, wherein said indole compound is to be administered orally.

6. The method of claim 1 or 2, wherein said indole compound is to be administered intramuscularly.

7. The method of claim 1 or 2, wherein said indole compound is to be administered 2, 3, 4 or 5 times a day.

8. The method of claim 1 or 2, wherein said indole compound is to be administered at a dose of from 1–20 mg every 4 hours.

9. The method of claim 1 or 2, wherein said indole compound is to be administered at a dose of 10 mg twice per day.

10. The method of claim 1 or 2, wherein said compound of formula I or II or pharmaceutically acceptable acid addition salt thereof is to be administered in a long lasting formulation.

11. The method of claim 10, wherein said compound of formula I or II or pharmaceutically acceptable acid addition salt of thereof is to be administered once daily.

12. The method of claim 10, wherein said compound of formula I or II or pharmaceutically acceptable acid addition salt thereof is to be administered at least once per week but less than once per day.

13. The method of claim 1 or 2, wherein said compound of formula I or II or pharmaceutically acceptable acid addition salt thereof is to be administered in the form of a patch.

14. The method of claim 1 or 2, wherein said compound of formula I or II or pharmaceutically acceptable acid addition salt thereof comprises the levorotatory enantiomer thereof in the absence of any substantial amount of the dextrorotatory enantiomer.

15. The method of claim 1 or 2, wherein said compound of formula I or II or pharmaceutically acceptable acid addition salt thereof is to be administered with another drug.

16. The method of claim 15, wherein said another drug is lithium.

17. A method of treating oppositional defiant disorder in a patient diagnosed therewith, wherein said method comprises administering a dihydroindoline analogue of compound I or II or a pharmaceutically acceptable acid salt of said analogue to said patient, wherein said compound I is represented by the general formula I,

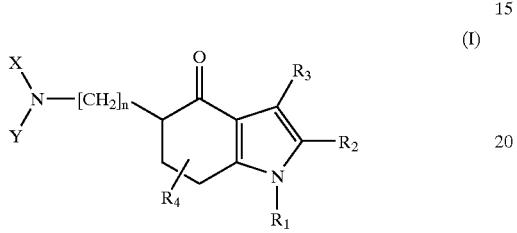

(I)

wherein:

n is 2 or 3;

$R_1$ designates hydrogen, a lower alkyl, benzyl, phenyl or 2-, 3- or 4-pyridyl;

$R_2$ and $R_3$ are each independently alkyl, alkenyl and cycloalkyl, phenyl, halogeno-phenyl or lower alkoxy phenyl;

$R_4$ designates hydrogen or a lower alkyl and being attached to carbon atom 6 or 7 of the indole nucleus; and X and Y designate lower alkyl, hydroxy lower alkyl, lower acyloxy alkyl, carbamoyloxy lower alkyl and phenyl lower alkyl or alternatively X and Y may be linked together and then constitute, together with the nitrogen atom to which they are attached, an NXY moiety that is an optionally substituted heterocyclic ring;

and wherein said compound II is represented by general formula II,

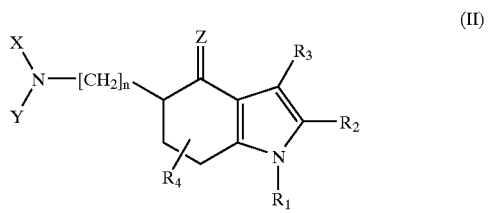

(II)

wherein:

n is 2 or 3;

$R_1$, $R_2$, $R_3$ and $R_4$ are each independently a hydrogen, alkyl, a alkenyl or a alkynyl radical optionally substituted by 1–3 radicals of amino, alkylamino, dialkylamino, alkanoylamino, alkoxycarbonylamino, alkylsulfonylamino, a hydrogen atom, hydroxy, alkoxy, alkylthio, an alkylsulfinyl group, a lower alkylsulfonyl group, halo, a carboxyl group, a lower alkoxy-carbonyl group, a benzyloxycarbonyl group, a cyano group, a benzyloxy group, a lower alkanoyloxy group, a cycloalkyl group, a cycloalkyl group, an aryl group, an aralkyl group, a substituted aryl group, a heteroaryl group, a substituted heteroaryl group, a benzenesulfonyloxy group being optionally substituted by an alkyl group; a lower alkanoylamino group, a lower alkoxycarbonylamino group, a lower alkylsulfonamido group, a phthalimido group;

or $R_3$ is also one or more members selected from the group consisting of hydrogen, amino, alkylamino, dialkylamino, alkanoylamino, alkoxycarbonylamino, and alkylsulfonylamido;

X and Y designate lower alkyl, hydroxy lower alkyl, lower acyloxy alkyl, carbamoyloxy lower alkyl and phenyl lower alkyl, or X and Y may be linked together and then constitute, together with the nitrogen atom to which they are attached, an NXY moiety that is an optionally substituted heterocyclic ring; and Z is selected from the group consisting of oxo, thio, seleno, telluro, and NH.

* * * * *